(12) United States Patent
Brunson et al.

(10) Patent No.: US 8,926,488 B2
(45) Date of Patent: Jan. 6, 2015

(54) HYPODERMIC NEEDLE CONTAINMENT SYSTEM

(76) Inventors: Robert W. Brunson, Ogden, UT (US); Jeremy Sorensen, West Jordan, UT (US)

(*) Notice: Subject to any disclaimer, the term of this patent is extended or adjusted under 35 U.S.C. 154(b) by 58 days.

(21) Appl. No.: 13/551,542

(22) Filed: Jul. 17, 2012

(65) Prior Publication Data

US 2014/0024876 A1    Jan. 23, 2014

(51) Int. Cl.
*B65D 85/10*   (2006.01)
*A61B 19/02*   (2006.01)

(52) U.S. Cl.
CPC .................. *A61B 19/0288* (2013.01)
USPC ....................... 588/249.5; 206/222

(58) Field of Classification Search
USPC ............. 588/252, 255, 249.5; 206/222
See application file for complete search history.

(56) References Cited

U.S. PATENT DOCUMENTS

| | | | | | |
|---|---|---|---|---|---|
| 1,332,985 | A | * | 3/1920 | Jarrett | 206/222 |
| 4,892,522 | A | * | 1/1990 | Suzuki et al. | 604/192 |
| 5,084,027 | A | * | 1/1992 | Bernard | 206/365 |
| 5,271,892 | A | * | 12/1993 | Hanson et al. | 206/366 |
| 5,322,165 | A | * | 6/1994 | Melker et al. | 206/366 |
| 5,988,371 | A | * | 11/1999 | Paley et al. | 206/229 |

* cited by examiner

*Primary Examiner* — John Kreck
(74) *Attorney, Agent, or Firm* — Michael F. Krieger; Kirton McConkie

(57) ABSTRACT

Containment systems and methods safely and permanently encapsulate a sharp portion of a sharp medical instrument (e.g. a hypodermic needle). The containment system includes a cap or other container formed of a durable and flexible material having a rim defining an open end configured to receive a sharp portion therein, an interior surface, wherein at least a portion of the interior surface comprises a puncturing element, and a bladder contained within the cap proximate the puncturing element, the bladder containing a first component of a liquid hardenable solution. Opposing sides of the cap can be deformed under external pressure to cause the puncturing element to puncture the bladder so as to release the first component of the liquid hardenable solution from the bladder such that the first component contacts the sharp portion and the sharp portion is substantially permanently retained inside the cap by the liquid hardenable solution.

17 Claims, 5 Drawing Sheets

HYPODERMIC NEEDLE CONTAINMENT SYSTEM

BACKGROUND OF THE INVENTION

1. Field of the Invention

The present invention relates to containment systems for hypodermic needles and other sharp medical instruments, and more particularly to containment systems permanently encapsulating and containing hypodermic needles to prevent reuse and accidental needle sticks.

2. Background and Related Art

The handling and disposal of used medical instruments, particularly sharp medical instruments such as hypodermic needles, suture needles, lancets, trocars, scalpel blades and the like is a major problem facing healthcare professionals. Blood-born pathogens can be easily transmitted by inadvertent contact with the used medical instrument such as by accidental needle sticks.

In order to avoid such accidental needle sticks, especially immediately after using the needle, the healthcare professional will attempt to cover the needle with a protective cap or sheath so that the instrument can be safely transported for disposal. The provision for caps and sheaths affords some degree of protection, however many accidental needle sticks occur while trying to place the cap or sheath back on the needle in preparation for transport for disposal.

In the absence of re-capping or re-sheathing, quite often the used medical instrument is transported uncovered to a sharps container which ideally is located proximate to the site. The sharps container holds several used medical instruments in a hard puncture-resistant package which is subsequently collected for final disposal. However, this still requires the healthcare professional to handle and transport the unprotected needle after use. Also, the collected used instruments remain on site in the sharps container until collected for final disposal.

The art has seen many devices for capping, closing and sheathing used sharp medical instruments for disposal. Many of these devices simply enclose the entire medical instrument, or at least the sharp portion thereof in a protective enclosure. Other of these devices attempt to encapsulate or surround the used medical instrument with a composition which hardens around the sharp portion of the instrument, providing permanent containment and protection.

One such encapsulation system uses a two-part hardenable compound provided in a container (e.g. a needle cover) which accepts a sharp medical instrument such as a hypodermic needle. The container supports a hardenable resin such as a cyanoacrylate ester and a filler of particulate matter in spaced separation. The filler includes an accelerator which is used to speed up the hardening of the resin. The resin and the filler accelerator are separated by a rupturable partition such as thin glass. The used medical instrument, such as a needle, is inserted into the container, rupturing the glass membrane between the two components, thereby causing the components to come together and harden around the needle.

Such encapsulation systems have several disadvantages. First, it can be difficult and hence expensive to properly manufacture such systems, as the small scale of such systems necessitates care and precision in manufacturing. If any manufacturing deficiencies allow the two-part hardenable compound to mix before the intended time, the attempt to insert the needle into the encapsulation system may fail, and an additional system will be needed. Additionally, such systems of necessity require two separate devices for protecting the hypodermic needle before and after use: a standard cap or cover for protecting the needle before use, and an encapsulation cap or cover for after use of the needle. The use of multiple caps or covers results in extra waste, extra costs, extra time spent seeking to ensure that the correct cap or cover is used, etc. Finally, such systems may be prone to inadequate mixing of the two-part hardenable compound, such that permanent encapsulation of the needle is not achieved.

BRIEF SUMMARY OF THE INVENTION

Implementations of the invention provide a containment system for encapsulating a sharp medical instrument. The containment system includes a container formed of a durable and flexible material having a rim defining an open end configured to receive a sharp portion of the medical instrument, an interior surface, wherein at least a portion of the interior surface comprises a puncturing element, and a bladder contained within the container proximate the puncturing element, the bladder containing a first component of a liquid hardenable solution. Opposing sides of the container can be deformed under external pressure to cause the puncturing element to puncture the bladder so as to release the first component of the liquid hardenable solution from the bladder such that the first component contacts the sharp portion and the sharp portion is substantially permanently retained inside the container by the liquid hardenable solution.

The sharp medical instrument may be a hypodermic needle. In some implementations, the bladder is a first bladder and the system includes a second bladder contained within the container, the second bladder containing a second component of the liquid hardenable solution. A second puncturing element disposed on the interior surface proximate the second bladder may serve to puncture the second bladder. Alternatively or additionally, the container may include a compound disposed on an interior surface of the container, the compound being configured to cause hardening of the liquid hardenable solution.

The container may have a cross-section having a major axis and a minor axis such that the container is deformable in the direction of the minor axis to permit opposite sides of the container to compress along the minor axis until the bladder is punctured by the puncturing element. The container may have a generally-oval cross section. The puncturing element may be a serrated element extending longitudinally along a portion of the interior surface.

Implementations of the invention provide a method for safely and permanently encapsulating a sharp medical instrument. The method may include inserting the sharp medical instrument into a container having a rim defining an open end configured to receive a sharp portion of the medical instrument, an interior surface, wherein at least a portion of the interior surface comprises a puncturing element, and a bladder contained within the container proximate the puncturing element, the bladder containing a first component of a liquid hardenable solution. The method further includes causing opposing sides of the container to be deformed under external pressure to cause the puncturing element to puncture the bladder so as to release the first component of the liquid hardenable solution from the bladder such that the first component contacts the sharp portion and the sharp portion is substantially permanently retained inside the container by the liquid hardenable solution.

In the method, the sharp medical instrument may be a hypodermic needle. The method may also include, before inserting the sharp medical instrument into the container, removing the sharp medical instrument from the container and using the sharp medical instrument.

The bladder may be a first bladder and the container may further include a second bladder within the container, the second bladder containing a second component of the liquid hardenable solution, the second bladder being configured to be punctured by the puncturing element or by another puncturing element disposed on the interior surface. In the method, the container may have a cross-section having a major axis and a minor axis, wherein the container is deformable in the direction of the minor axis to permit opposite sides of the container to compress along the minor axis until the bladder is punctured by the puncturing element.

Implementations of the invention provide a containment system for encapsulating a hypodermic needle. The containment system includes a cap formed of a durable and flexible material having a rim defining an open end configured to receive a sharp portion of the hypodermic needle, an interior surface, wherein at least a portion of the interior surface comprises a puncturing element, and a bladder contained within the cap proximate the puncturing element, the bladder containing a first component of a liquid hardenable solution. Opposing sides of the cap can be deformed under external pressure to cause the puncturing element to puncture the bladder so as to release the first component of the liquid hardenable solution from the bladder such that the first component contacts the sharp portion and the sharp portion is substantially permanently retained inside the cap by the liquid hardenable solution.

The bladder may be a first bladder and the system may include a second bladder contained within the cap, the second bladder containing a second component of the liquid hardenable solution. A second puncturing element may be disposed on the interior surface proximate the second bladder. Alternatively or additionally, the cap further includes a compound disposed on an interior surface of the cap, the compound being configured to cause hardening of the liquid hardenable solution.

The cap may have a cross-section having a major axis and a minor axis, wherein the cap is deformable in the direction of the minor axis to permit opposite sides of the cap to compress along the minor axis until the bladder is punctured by the puncturing element. The cap may have a generally-oval cross section. The puncturing element may include a serrated element extending longitudinally along a portion of the interior surface.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

Figure 1:
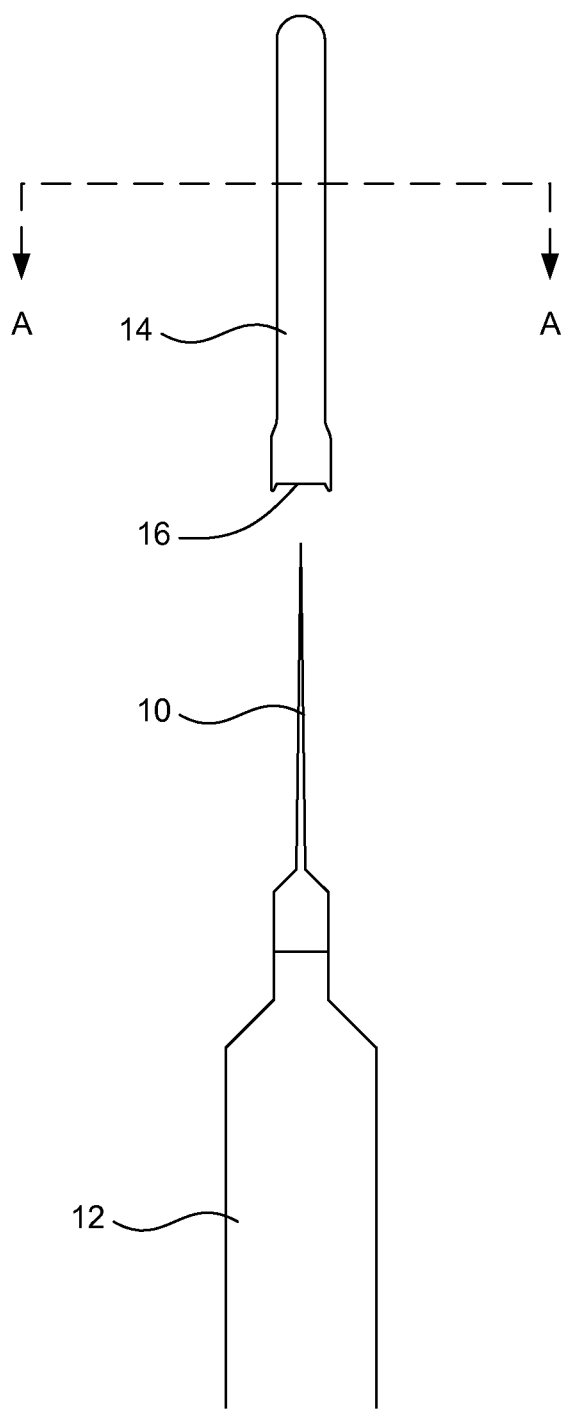
FIG. 1 shows a plan view of a representative hypodermic needle and cap.

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Embodiments of the invention provide a containment system for encapsulating a sharp medical instrument. The containment system includes a container formed of a durable and flexible material having a rim defining an open end configured to receive a sharp portion of the medical instrument, an interior surface, wherein at least a portion of the interior surface comprises a puncturing element, and a bladder contained within the container proximate the puncturing element, the bladder containing a first component of a liquid hardenable solution. Opposing sides of the container can be deformed under external pressure to cause the puncturing element to puncture the bladder so as to release the first component of the liquid hardenable solution from the bladder such that the first component contacts the sharp portion and the sharp portion is substantially permanently retained inside the container by the liquid hardenable solution.

The sharp medical instrument may be a hypodermic needle. In some embodiments, the bladder is a first bladder and the system includes a second bladder contained within the container, the second bladder containing a second component of the liquid hardenable solution. A second puncturing element disposed on the interior surface proximate the second bladder may serve to puncture the second bladder. Alternatively or additionally, the container may include a compound disposed on an interior surface of the container, the compound being configured to cause hardening of the liquid hardenable solution.

The container may have a cross-section having a major axis and a minor axis such that the container is deformable in the direction of the minor axis to permit opposite sides of the container to compress along the minor axis until the bladder is punctured by the puncturing element. The container may have a generally-oval cross section. The puncturing element may be a serrated element extending longitudinally along a portion of the interior surface.

Embodiments of the invention provide a method for safely and permanently encapsulating a sharp medical instrument. The method may include inserting the sharp medical instrument into a container having a rim defining an open end configured to receive a sharp portion of the medical instrument, an interior surface, wherein at least a portion of the interior surface comprises a puncturing element, and a bladder contained within the container proximate the puncturing element, the bladder containing a first component of a liquid hardenable solution. The method further includes causing opposing sides of the container to be deformed under external pressure to cause the puncturing element to puncture the bladder so as to release the first component of the liquid hardenable solution from the bladder such that the first component contacts the sharp portion and the sharp portion is substantially permanently retained inside the container by the liquid hardenable solution.

In the method, the sharp medical instrument may be a hypodermic needle. The method may also include, before inserting the sharp medical instrument into the container, removing the sharp medical instrument from the container and using the sharp medical instrument.

The bladder may be a first bladder and the container may further include a second bladder within the container, the second bladder containing a second component of the liquid hardenable solution, the second bladder being configured to be punctured by the puncturing element or by another puncturing element disposed on the interior surface. In the method, the container may have a cross-section having a major axis and a minor axis, wherein the container is deformable in the direction of the minor axis to permit opposite sides of the container to compress along the minor axis until the bladder is punctured by the puncturing element.

Embodiments of the invention provide a containment system for encapsulating a hypodermic needle. The containment system includes a cap formed of a durable and flexible material having a rim defining an open end configured to receive a sharp portion of the hypodermic needle, an interior surface, wherein at least a portion of the interior surface comprises a puncturing element, and a bladder contained within the cap proximate the puncturing element, the bladder containing a first component of a liquid hardenable solution. Opposing sides of the cap can be deformed under external pressure to cause the puncturing element to puncture the bladder so as to release the first component of the liquid hardenable solution from the bladder such that the first component contacts the sharp portion and the sharp portion is substantially permanently retained inside the cap by the liquid hardenable solution.

The bladder may be a first bladder and the system may include a second bladder contained within the cap, the second bladder containing a second component of the liquid hardenable solution. A second puncturing element may be disposed on the interior surface proximate the second bladder. Alternatively or additionally, the cap further includes a compound disposed on an interior surface of the cap, the compound being configured to cause hardening of the liquid hardenable solution.

The cap may have a cross-section having a major axis and a minor axis, wherein the cap is deformable in the direction of the minor axis to permit opposite sides of the cap to compress along the minor axis until the bladder is punctured by the puncturing element. The cap may have a generally-oval cross section. The puncturing element may include a serrated element extending longitudinally along a portion of the interior surface.

FIG. 1 illustrates one system for encapsulating a sharp portion of a sharp medical instrument, namely a hypodermic needle 10 affixed to a syringe 12. The needle 10 and syringe 12 are in all respects essentially identical to known syringes and needles, and permit delivery of liquids from the syringe 12 through a hollow channel of the needle 10 into a target tissue, vessel, etc. As with any needle, it is desirable to prevent accidental needle sticks of the needle 10 before and after the needle 10 is to be used, and it is also desirable to prevent re-use of the needle 10 after its initial intended use to prevent the spread of blood-borne pathogens and the like. It is also desirable to prevent re-use of the needle 10, as re-use is commonly associated with illicit drug use, and is therefore even more likely to be associated with pathogen transmission.

Therefore, associated with the needle 10 and the syringe 12 is a cap 14, which is one example of a container for receiving a sharp portion of a sharp medical instrument. As with standard syringe caps, the cap 14 is sized and formed so as to be removably affixable to the syringe 12 covering the needle 10. The cap 14 may be affixable to the syringe 12 using any known system or method, including a snap fit, a frictional engagement, or a threaded engagement between the cap 14 and the syringe 12.

The cap 14 may be constructed in many ways similarly to known caps, covers, and containers for syringes, and may be made, for example, of a durable but deformable plastic material. The cap 14 may typically be provided covering the needle 10, either with the syringe 12 or as a needle system to be affixed to the syringe 12, as is typically done with existing needle and cap or needle, syringe and cap systems. Thus, embodiments of the invention may be advantageously used in conjunction with existing needles and syringes in all respects without modification to the existing needles and syringes, and without requiring the use of multiple caps for each needle and syringe.

Figure 2:
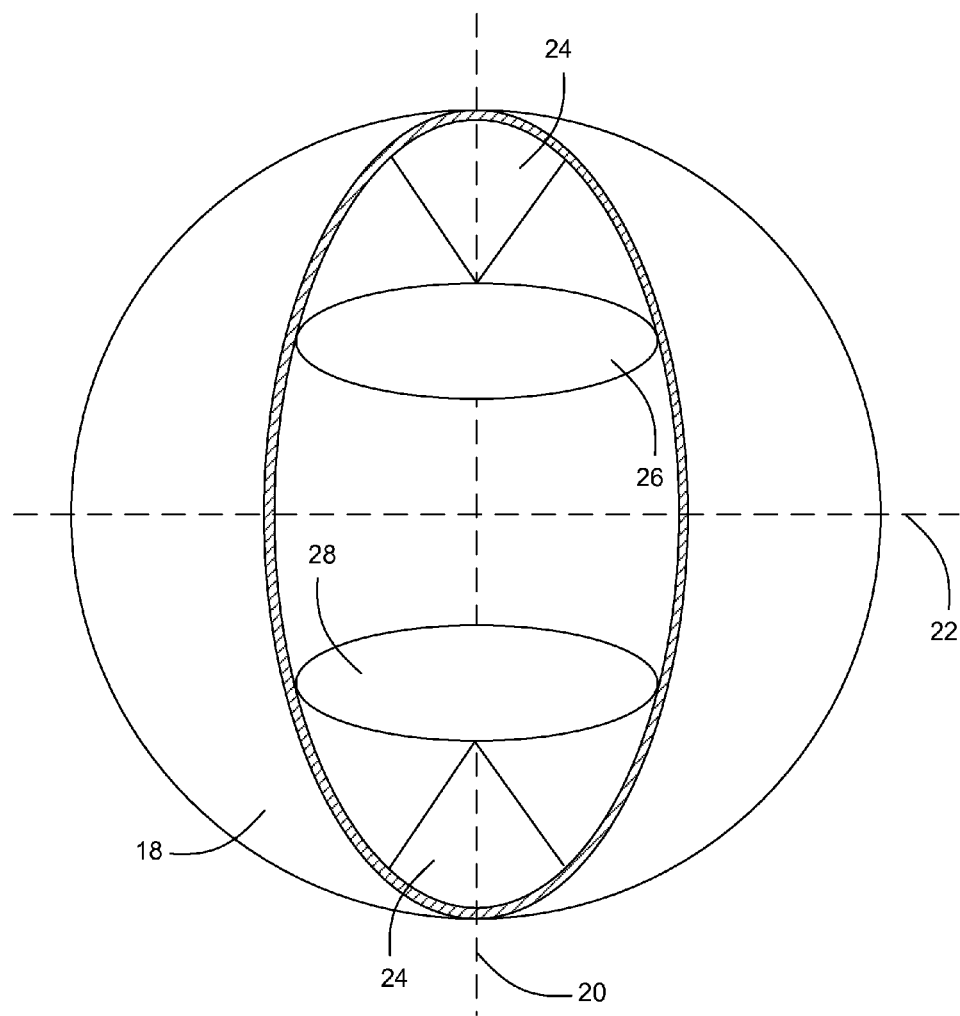
FIG. 2 shows a cross-sectional view of a representative cap.

The cap 14 includes a rim 16 defining an open end of the cap 14, the open end being configured to receive the needle 10 into the cap 14. FIG. 2 shows a cross-sectional view of one embodiment of the cap 14, taken along the line A-A shown in FIG. 1. As may be seen in FIG. 2, the cap 14 has a round base 18 for engaging a round portion of the syringe 12; however, at the location of the cross section, the cap 14 may have a generally-oval cross section, with a major axis 20 and a minor axis 22. Because the cap 14 is made of a deformable material, the cap 14 is deformable in the direction of the minor axis 22 such that opposing walls or sides of the cap 14 may be deformed under pressure. Disposed on an interior surface of the deformable portion of the cap 14 is a puncturing element 24. The puncturing element 24 may be disposed on opposite sides of the deformable portion of the cap as is shown in FIG. 2. Disposed adjacent one of the puncturing elements 24 is a first bladder 26 which contains a first component of a liquid hardenable solution. Similarly, disposed adjacent the other puncturing element 24 is a second bladder 28 which contains a second component of the liquid hardenable solution. When the deformable portion of the cap 14 is deformed by external inwardly-directed pressure along the major axis 20, the puncturing elements 24 puncture the first bladder 26 and the second bladder 28, thereby releasing the first and second components of the liquid hardenable solution, which mix around the hypodermic needle 10, thereby trapping and containing the needle 10 therein. This containment prevents needle sticks and re-use of the needle 10.

Figure 3:
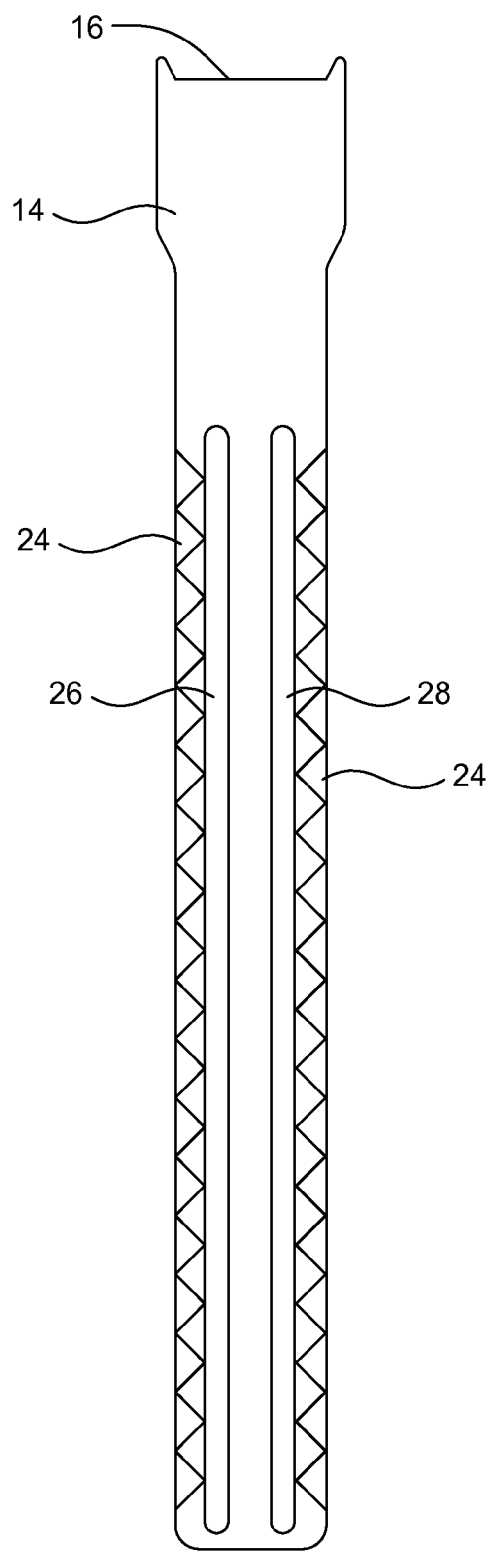
FIG. 3 shows a plan view of a representative cap.
Figure 4:
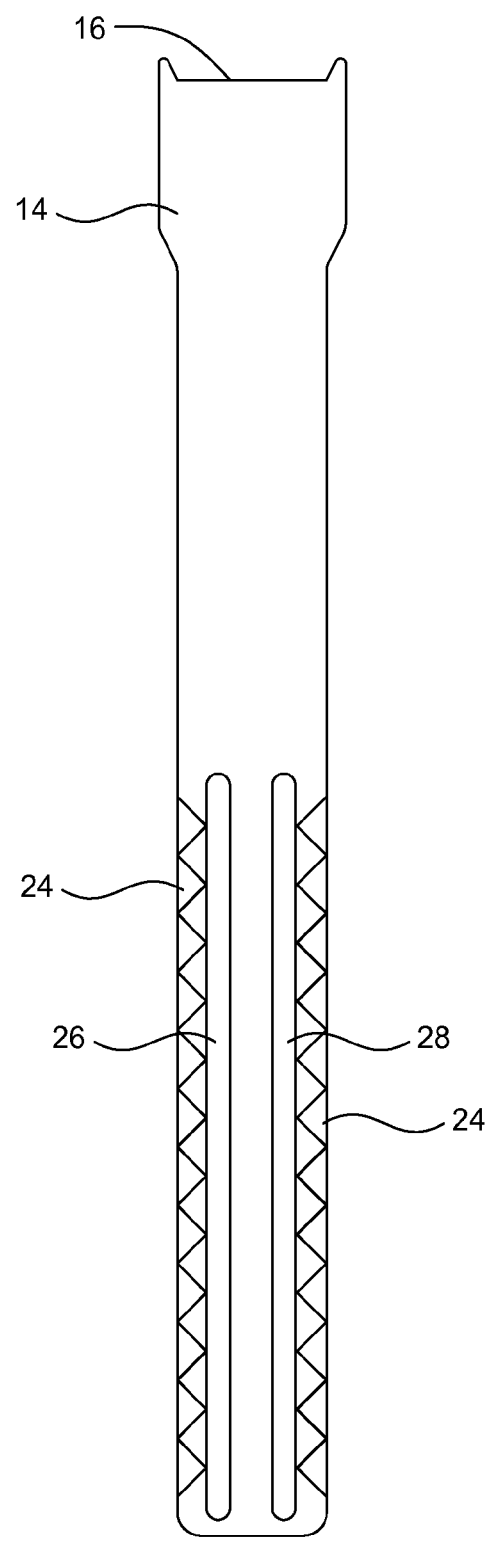
FIG. 4 shows a plan view of an alternative representative cap.
Figure 5:
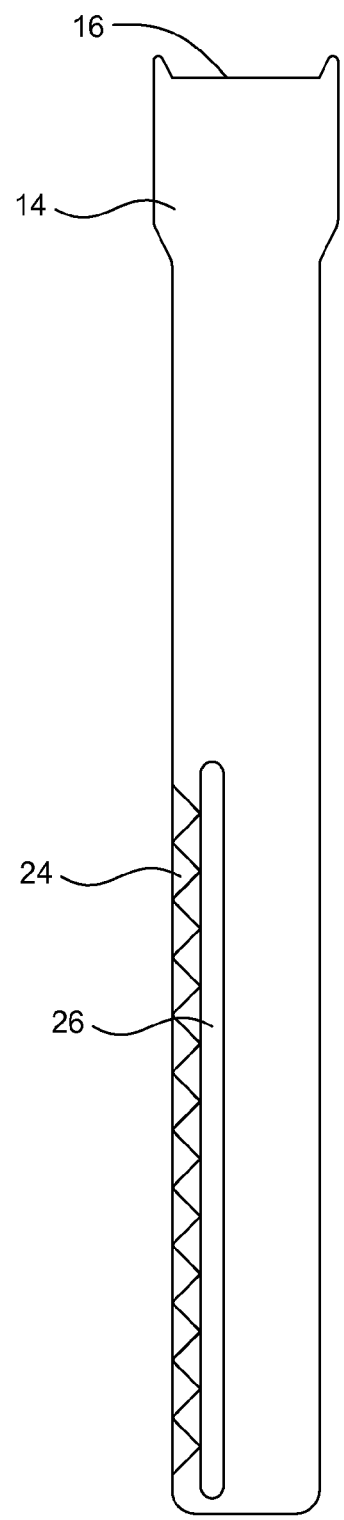
FIG. 5 shows a plan view of another alternative representative cap.

FIGS. 3-5 show plan views of representative embodiments of the cap 14. In the embodiment of FIG. 3, the cap 14 includes two puncturing elements 24 that extend longitudinally along opposite interior sides of a major portion of the length of the cap 14, forming serrated edges that puncture the first bladder 26 and the second bladder 28, regardless of where along the length of the cap 14 the user squeezes the cap 14. In the embodiment of FIG. 4, the cap 14 also includes two puncturing elements 24 that serve to puncture the first bladder 26 and the second bladder 28, but the puncturing elements 24, the first bladder 26, and the second bladder 28 are only disposed along a distal portion of the cap 14 near where the tip of the needle 10 typically resides. As long as the tip of the needle 10 is encapsulated, reuse of the needle 10 will be prevented.

In the embodiment of FIG. 5, the puncturing element 24 is disposed on only a single side of the cap 14 and only the first bladder 26 is present. In this embodiment, the first component of the liquid hardenable solution is contained in the first bladder 26 and is either activated (to cause hardening) by exposure to air upon rupturing of the first bladder 26 by the puncturing element 24, or is activated by exposure to a second component of the liquid hardenable solution that is disposed on the internal surface of the cap 14 proximate the first bladder 26, such as on the puncturing element 24.

Regardless of the embodiment, the use of the various embodiments is similar, with the cap 14 being initially included with and covering the needle 10. The cap 14 is then removed and the needle 10 used, such as with the syringe 12, whereupon the needle is re-inserted into the cap 14. Because re-use of the needle 10 is to be prevented in any case, no regard need be taken as to whether the needle 10 encounters or ruptures one or both of the first bladder 26 and the second bladder 28. Regardless of whether one of the bladders 26, 28 has been ruptured, the user squeezes the sides of the cap 14 in the direction of the major axis 20 at a location where the puncturing elements 14 are located, thereby ensuring the bladder 26 or bladders 26, 28 have been ruptured, and the liquid hardenable solution encases and hardens around the needle 10, substantially permanently encapsulating it to prevent reuse or accidental needle sticks.

While embodiments of the invention have been shown with relation to squeezing or crushing the cap 14 along the major axis 20 to encapsulate the needle 10, it will be understood that the components illustrated may be located so as to permit crushing or squeezing the cap 14 along the minor axis 20 to the same effect.

Since at least some of the materials forming the liquid hardenable solution are liquid, some of the combined material may actually flow into the hollow interior channel of the needle 10. This results in plugging the interior channel further rendering the needle 10 non-reusable.

The admixing of the liquid hardenable solution components causes encapsulation of the needle 10 rapidly, and desirably within a matter of seconds. Useful hardenable solutions are known in the art and include, for example, any liquid resin which when admixed with a liquid resin hardener cures in a sufficiently rapid time to be commercially acceptable for the devices and methods of embodiments of the present invention. For example, an acceptable hardening time may be between about 20 seconds to about 40 seconds. Useful resins include anaerobically curable resins, polyurethane polyacrylate resins, epoxy resins, cyanoacrylates, vinyl resins, silicone resins, and silicone-acrylate resins. Combinations and copolymers of such resin materials are also useful.

For example, useful anaerobically curable resins include those based on mono- and poly(meth)acrylate monomers. Examples of resin hardeners useful with anaerobic curing resins include solutions of metal salts. The use of salt solutions facilitates the mixing of the resin hardener with the hardenable resin to obtain rapid hardening. Virtually any transition metal salt solution may be employed, such as salt solutions of copper, iron, nickel and zinc. Examples of useful copper salts include copper octonate and the diketone salts of copper. Accelerators typically employed with anaerobic systems may also be incorporated in the resin hardener component. Amines are frequently used as accelerators in compatible organic carriers, such as tetraethylene glycol esters. Amines may be effectively combined with saccharin. Hydrazine derivatives and sulfonamides are also useful as accelerators. Useful cyanoacrylate resins may employ amines, thiols, or benzothiazole sulfenamide derivatives as resin hardeners.

Epoxy resins may be used with typical resin hardeners for epoxies, such as amines or thiol compounds. Conventional proportions of resin to resin hardener may be employed, depending on the particular components, as is known in the art.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A containment system for encapsulating a sharp medical instrument comprising:
    a container formed of a durable and flexible material comprising:
        a rim defining an open end configured to receive a sharp portion of the medical instrument;
        an interior surface, wherein at least a portion of the interior surface comprises a puncturing element comprising a serrated element extending longitudinally along a portion of the interior surface; and
        a bladder contained within the container proximate the puncturing element, the bladder containing a first component of a liquid hardenable solution;
    wherein opposing sides of the container can be deformed under external pressure to cause the puncturing element to puncture the bladder so as to release the first component of the liquid hardenable solution from the bladder such that the first component contacts the sharp portion and the sharp portion is substantially permanently retained inside the container by the liquid hardenable solution.

2. A containment system as recited in claim 1, wherein the sharp medical instrument comprises a hypodermic needle.

3. A containment system as recited in claim 1, wherein the bladder is a first bladder and the system further comprises a second bladder contained within the container, the second bladder containing a second component of the liquid hardenable solution.

4. A containment system as recited in claim 3, wherein the system further comprises a second puncturing element disposed on the interior surface proximate the second bladder.

5. A containment system as recited in claim 1, wherein the container comprises a cross-section having a major axis and a minor axis, and wherein the container is deformable in the direction of the minor axis to permit opposite sides of the container to compress along the minor axis until the bladder is punctured by the puncturing element.

6. A containment system as recited in claim 5, wherein the container comprises a generally-oval cross section.

7. A containment system as recited in claim 1, wherein the container further comprises a compound disposed on an interior surface of the container, the compound being configured to cause hardening of the liquid hardenable solution.

8. A method for safely and permanently encapsulating a sharp medical instrument, the method comprising:
    removing the sharp medical instrument from a container, the container comprising:
        a rim defining an open end configured to receive a sharp portion of the medical instrument;
        an interior surface, wherein at least a portion of the interior surface comprises a puncturing element; and
        a bladder contained within the container proximate the puncturing element, the bladder containing a first component of a liquid hardenable solution;
    using the sharp medical instrument;
    inserting the sharp medical instrument into the container; and
    causing opposing sides of the container to be deformed under external pressure to cause the puncturing element to puncture the bladder so as to release the first component of the liquid hardenable solution from the bladder such that the first component contacts the sharp portion and the sharp portion is substantially permanently retained inside the container by the liquid hardenable solution.

9. A method as recited in claim 8, wherein the sharp medical instrument comprises a hypodermic needle.

10. A method as recited in claim 8, wherein the bladder is a first bladder and the container further comprises a second bladder within the container, the second bladder containing a second component of the liquid hardenable solution, the second bladder being configured to be punctured by the puncturing element or by another puncturing element disposed on the interior surface.

11. A method as recited in claim 8, wherein the container comprises a cross-section having a major axis and a minor axis, and wherein the container is deformable in the direction of the minor axis to permit opposite sides of the container to compress along the minor axis until the bladder is punctured by the puncturing element.

12. A containment system for encapsulating a hypodermic needle comprising:
   a cap formed of a durable and flexible material comprising:
      a rim defining an open end configured to receive a sharp portion of the hypodermic needle;
      an interior surface, wherein at least a portion of the interior surface comprises a puncturing element comprising a serrated element extending longitudinally along a portion of the interior surface; and
      a bladder contained within the cap proximate the puncturing element, the bladder containing a first component of a liquid hardenable solution;
   wherein opposing sides of the cap can be deformed under external pressure to cause the puncturing element to puncture the bladder so as to release the first component of the liquid hardenable solution from the bladder such that the first component contacts the sharp portion and the sharp portion is substantially permanently retained inside the cap by the liquid hardenable solution.

13. A containment system as recited in claim 12, wherein the bladder is a first bladder and the system further comprises a second bladder contained within the cap, the second bladder containing a second component of the liquid hardenable solution.

14. A containment system as recited in claim 13, wherein the system further comprises a second puncturing element disposed on the interior surface proximate the second bladder.

15. A containment system as recited in claim 12, wherein the cap comprises a cross-section having a major axis and a minor axis, and wherein the cap is deformable in the direction of the minor axis to permit opposite sides of the cap to compress along the minor axis until the bladder is punctured by the puncturing element.

16. A containment system as recited in claim 15, wherein the cap comprises a generally-oval cross section.

17. A containment system as recited in claim 12, wherein the cap further comprises a compound disposed on an interior surface of the cap, the compound being configured to cause hardening of the liquid hardenable solution.

* * * * *